(12) United States Patent
Pirovic

(10) Patent No.: US 7,816,849 B2
(45) Date of Patent: Oct. 19, 2010

(54) GERMICIDAL LOW PRESSURE MERCURY VAPOR DISCHARGE LAMP WITH AMALGAM LOCATION AND TEMPERATURE CONTROL PERMITTING HIGH OUTPUT

(75) Inventor: Arpad Pirovic, Woodbridge, CT (US)

(73) Assignee: Light Sources, Inc., Orange, CT (US)

( * ) Notice: Subject to any disclaimer, the term of this patent is extended or adjusted under 35 U.S.C. 154(b) by 992 days.

(21) Appl. No.: 11/496,343

(22) Filed: Jul. 31, 2006

(65) Prior Publication Data

US 2006/0267495 A1    Nov. 30, 2006

Related U.S. Application Data

(63) Continuation-in-part of application No. 10/406,759, filed on Apr. 3, 2003, now Pat. No. 7,095,167.

(51) Int. Cl.
*H01J 61/20* (2006.01)
(52) U.S. Cl. ............... 313/490; 313/13; 313/639
(58) Field of Classification Search ............ 313/13, 313/490, 639
See application file for complete search history.

(56) References Cited

U.S. PATENT DOCUMENTS

| | | | | |
|---|---|---|---|---|
| 3,336,502 A | * | 8/1967 | Gilliatt | 315/108 |
| 3,851,207 A | * | 11/1974 | McVey | 315/49 |
| 4,471,225 A | | 9/1984 | Hillman | 250/436 |
| 4,700,101 A | | 10/1987 | Ellner et al. | |
| 4,794,301 A | * | 12/1988 | Misono et al. | 313/490 |
| 4,968,891 A | | 11/1990 | Jhawar et al. | 250/438 |

(Continued)

FOREIGN PATENT DOCUMENTS

WO    WO 96/31902    10/1996

OTHER PUBLICATIONS

IESNA Light Sources Committee, Understanding and controlling the effects of temperature on fluorescent lamp systems, 1996, pp. 1-11.

(Continued)

*Primary Examiner*—Nimeshkumar D Patel
*Assistant Examiner*—Christopher M Raabe
(74) *Attorney, Agent, or Firm*—Fattibene and Fattibene; Paul A. Fattibene

(57) ABSTRACT

A germicidal lamp having amalgam for controlling mercury vapor pressure contained in a location facilitating efficient high output operation. A low pressure mercury vapor discharge lamp has an amalgam container containing an amalgam positioned behind an electrode out of the arc path or space. The amalgam position is retained during high wall loading of the lamp preventing the amalgam from moving out of position. A heating and cooling element is placed generally at the amalgam position controlling the temperature of the amalgam. Efficient operation with high current loads and resulting high wall loading and temperatures is possible. The temperature control of the amalgam may also be used to dim or modify the illumination output of the lamp. The germicidal lamp is particularly suited to being positioned vertically in a waste water treatment system.

13 Claims, 5 Drawing Sheets

U.S. PATENT DOCUMENTS

| | | |
|---|---|---|
| 5,274,305 A * | 12/1993 | Bouchard .................... 315/108 |
| 5,294,867 A | 3/1994 | Grossman |
| 5,352,359 A | 10/1994 | Nagai et al. ................. 210/192 |
| 5,757,129 A | 5/1998 | Schafnitzel et al. |
| 6,172,452 B1 * | 1/2001 | Itaya et al. .................. 313/490 |
| 6,310,437 B1 | 10/2001 | Blau et al. .................. 313/552 |
| 6,337,539 B1 | 1/2002 | Yorifuji et al. |
| 6,404,122 B1 | 6/2002 | Lankhorst et al. |

OTHER PUBLICATIONS

J. Bloem et al, Some new mercury alloys for use in fluorescent lamps, Apr. 1977, Journal of Illuminating Engineering Society, pp. 141-147.

* cited by examiner

GERMICIDAL LOW PRESSURE MERCURY VAPOR DISCHARGE LAMP WITH AMALGAM LOCATION AND TEMPERATURE CONTROL PERMITTING HIGH OUTPUT

RELATED APPLICATION

This application is a continuation-in-part application of application Ser. No. 10/406,759, filed Apr. 3, 2003, now U.S. Pat. No. 7,095,167 which is herein incorporated by reference.

FIELD OF THE INVENTION

The present invention relates generally to low pressure mercury vapor discharge germicidal lamps used to disinfect or purify fluids, and more particularly to a germicidal lamp having a structure permitting high output and relatively high temperature operation.

BACKGROUND OF THE INVENTION

Low pressure mercury vapor discharge lamps are commonly used to generate ultraviolet radiation and used to irradiate a fluid to kill potentially harmful organisms contained in the fluid. Often, relatively high doses of ultraviolet radiation are required. The necessary relatively high doses of ultraviolet radiation typically require the use of multiple germicidal lamps. The use of multiple germicidal lamps increases expenses, as well as maintenance. Therefore, it is desirable to use fewer higher output germicidal lamps. However, producing a high output germicidal lamp is not without difficulties. During operation of a low pressure mercury vapor discharge lamp, the vapor pressure of the mercury greatly affects lamp operation. A predetermined vapor pressure is desirable for efficient operation of the lamp. However, under heavy loads used to produce a high output, mercury vapor pressure may increase reducing the efficiency and operation of the lamp. Amalgam has often been used to control the mercury vapor pressure within the lamp, permitting the lamp to operate more efficiently. However, the higher temperatures occurring at high loading of the lamp often cause the amalgam to melt. If the amalgam melts, it will move out of position and could make contact with an electrode and cause possible shorting or ineffective operation of the lamp.

A germicidal lamp using an amalgam is disclosed in Patent Cooperation Treaty international application No. PCT/DE96/00647 having a publication number of WO96/31902 and published Oct. 10, 1996, entitled "Low Pressure Mercury Vapor Discharge Lamp". Therein disclosed is a low pressure mercury vapor discharge lamp having an amalgam placed along the inner wall between the electrodes. The lamp tube is in mechanical contact with a cooler on the outside of the lamp adjacent the location of the amalgam. While this lamp structure is helpful in keeping the amalgam cool and therefore permitting higher loading of the lamp to improve output, the amalgam could still melt causing the amalgam to move out of position. This is particularly problematic in applications where the lamp is held vertically rather than horizontally, which could result in the amalgam falling downward onto one of the electrodes.

Therefore, there is a need for a low pressure mercury vapor discharge germicidal lamp for producing a high output of ultraviolet radiation that reduces the possibility of an amalgam melting or moving out of a desired location during high loading.

SUMMARY OF THE INVENTION

The present invention relates to a germicidal low pressure mercury vapor discharge lamp for operating under a high load having improved operation and output. An amalgam is positioned out of the arc path during operation of the lamp. An amalgam container is positioned behind the electrode in a relatively cool location or cold spot. The amalgam container is open, permitting the surface of the amalgam to be exposed to the interior space of the lamp, yet restricted to prevent the amalgam from moving out of position from behind the electrode where it is out of the arc path.

One embodiment comprises a germicidal lamp system having a plurality of elongated lamps held vertically within a fluid. The amalgam container holds amalgam in a location behind the electrode preventing the amalgam from moving out of position during high loading of the germicidal lamps. The positioning of the amalgam in a cooler location makes possible the higher loading of the germicidal lamp.

Accordingly, it is an object of the present invention to provide a high output germicidal lamp capable of operating at high wall loads.

It is another object of the present invention to provide a germicidal lamp that is capable of using amalgams that may melt at the internal operating temperature of the germicidal lamp.

It is another object of the present invention to provide a germicidal lamp that can effectively operate over a wide temperature range.

It is another object of an embodiment of the present invention to control operation of the germicidal lamp.

It is an advantage of the present invention that the germicidal lamp can be held vertically during operation.

It is another advantage of the present invention that the amalgam is held in a cooler location outside of the arc path or positive column.

It is an advantage of an embodiment of the present invention that the vapor pressure within the germicidal lamp can be controlled.

It is a feature of the present invention that the amalgam is held in a position behind an electrode.

It is another feature of the present invention that a container is used to prevent the amalgam from moving out of a desired position.

It is a feature of an embodiment of the present invention that a heating and cooling element is used to control the amalgam temperature.

These and other objects, advantages, and features will become readily apparent in view of the following more detailed description.

DETAILED DESCRIPTION OF THE PREFERRED EMBODIMENTS

Figure 1:
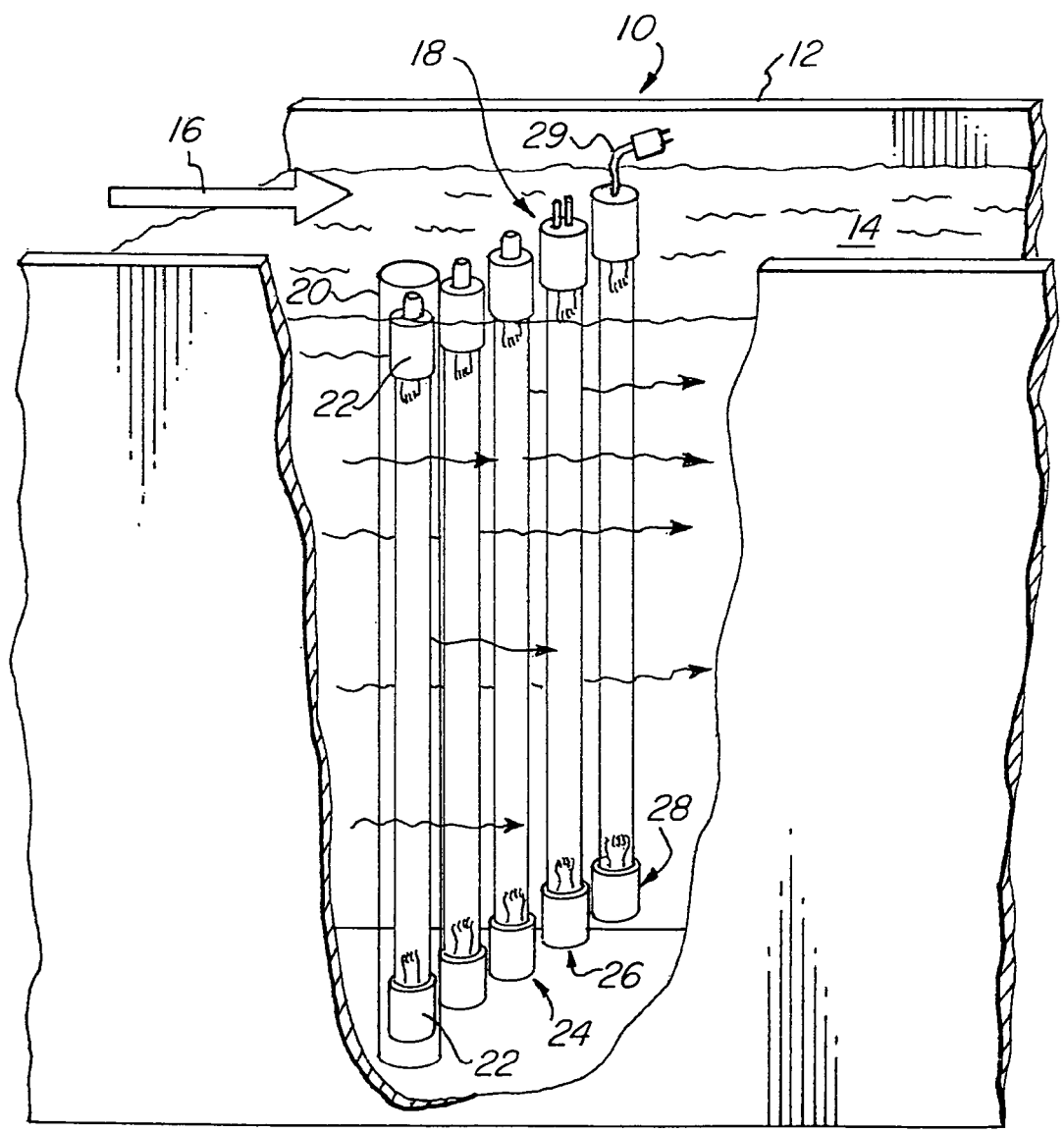
FIG. 1 schematically illustrates a plurality of germicidal lamps and a germicidal system according to the present invention.

FIG. 1 schematically illustrates a germicidal system 10 of the present invention. A container 12 holds a fluid 14 therein. The fluid may be waste water, air, or any other fluid type material that is to be purified or disinfected using ultraviolet radiation. The fluid or waste water 14 flows in the direction indicated by arrow 16. A plurality of germicidal lamps 18 are vertically placed within the fluid 14. Each of the plurality of lamps 18 may have a variety of different configurations. By way of example, several differently configured germicidal lamps are shown for illustrative purposes. Additionally, each of the germicidal lamps 18 may be placed in a protective sleeve 20. At each end of the lamp, end caps 22 are placed. The end caps 22 may be made of a plastic material and sealed against the glass tube of the germicidal lamp. The germicidal lamp may be sealed within the protective sleeve 20 by rubber seals or any other equivalent or conventional technique. For illustration purposes, a double ended lamp 24 is shown. The double ended lamp 24 has electrical connections or pins at either end of the lamp. A single ended lamp 26 may also be used. The single ended lamp 26 has two pins on one end for connecting to an electrical power source with a conductive wire extending along the length of the lamp to form an electrical connection with an electrode at the opposite end of the germicidal lamp. Such a single ended lamp 26 is more fully disclosed in U.S. Pat. No. 4,700,101 entitled "Elongated Tubular Lamp Construction" and issuing to Ellner et al on Oct. 13, 1987, which is herein incorporated by reference. The germicidal lamp may also be a single ended pigtail type lamp 28. The single ended pigtail lamp 28 has a pigtail 29 attached to the electrical terminals of the electrodes to facilitate an electrical connection. The pigtail 29 comprises flexible wires electrically attached or coupled to the electrodes and a connector having pins for connecting to a power source. Any conventional or equivalent electrical connection may be made with different types of germicidal lamps, as is well known.

In a germicidal lamp held vertically within a fluid column, it is often desirable to operate the germicidal lamp at high wall loading to improve output. The high wall loading may be greater than 250 milliwatts per centimeter squared. Comparatively, a conventional fluorescent lamp is generally only operated at a wall load of about 100 milliwatts per centimeter squared. During high current operation, with the resulting high wall load, the internal temperature of the lamp may increase to greater than 140° centigrade. At these temperatures, the mercury vapor pressure within the germicidal lamp increases to unacceptable levels. In order to keep the mercury vapor pressure within predetermined limits for effective operation of the lamps, amalgams are used to absorb and release mercury as required to maintain efficient operation. However, at high temperatures, the amalgam may melt, limiting their effectiveness and causing them to move out of position within the germicidal lamp. The present invention positions the amalgam outside of the arc path or outside of the positive column at a location behind the electrode in a cooler spot. The amalgam is positioned at a location where the internal temperature or wall temperature of the germicidal lamp is less than about 140° centigrade, even under high load. The location of the amalgam and containing the amalgam within the location permits efficient operation of the germicidal lamp at higher loading, and resulting higher temperatures. Additionally, by containing the amalgam in a restricted location yet open to the interior of the germicidal lamp, the amalgam may function effectively but be retained in the desired location if the amalgam melts during the high temperature occurring during high wall loads. This is particularly important in a germicidal application where the germicidal lamp is held vertically. Unless the amalgam is held in position according to the present invention, it would fall out of position upon melting and could possibly contact an electrode, greatly shortening the life of the germicidal lamp.

Additionally, different amalgams may be utilized that may melt at the internal operating temperatures therein improving operating efficiencies. The germicidal lamp of the present invention is capable of operating at external wall temperatures ranging from about 40° C. to 140° C. This temperature range is particularly advantageous in a germicidal lamp submerged in a liquid where the temperature of the liquid may vary. Accordingly, the present invention is particularly well suited and solves problems associated with germicidal lamps vertically positioned and operated under high loads.

Figure 2B:
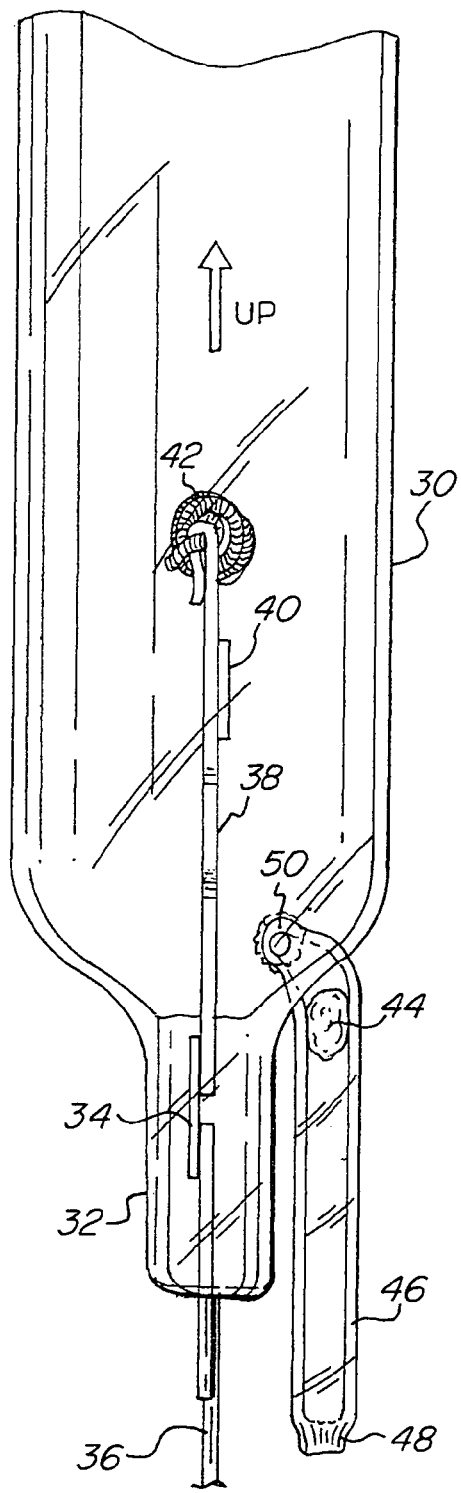
FIG. 2B illustrates the end portion of the germicidal lamp illustrated in FIG. 2A rotated 90°.
Figure 2A:
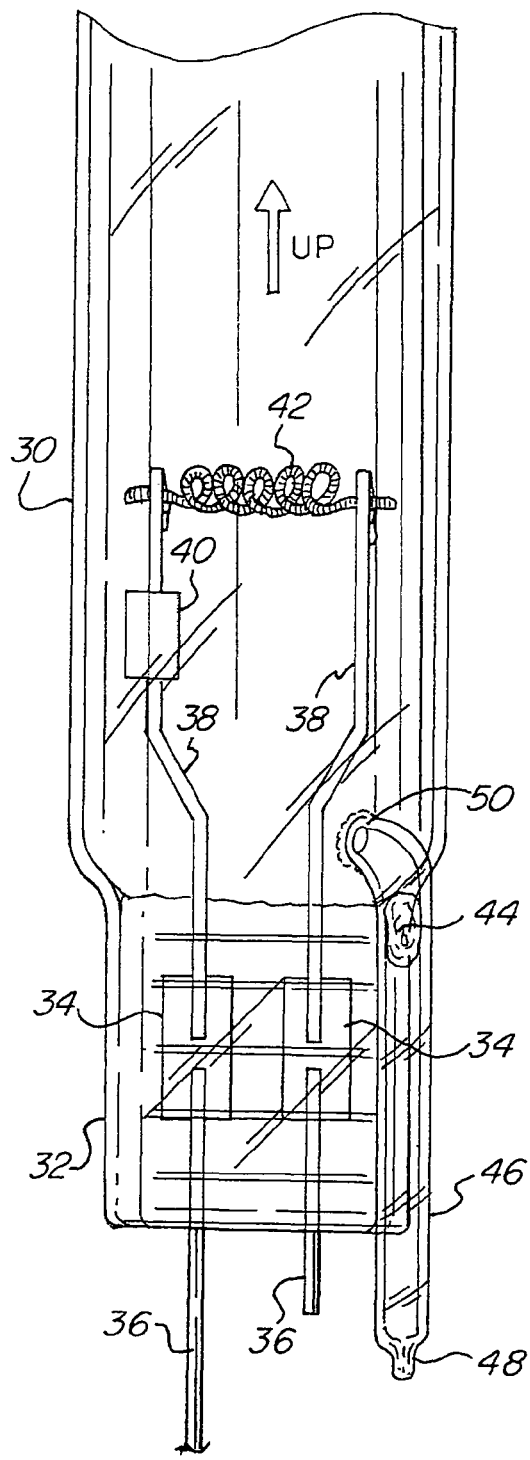
FIG. 2A is a partial view illustrating one end of a germicidal lamp according to the present invention.

FIG. 2A illustrates one end of one of the plurality of germicidal lamps 18 illustrated in FIG. 1. The opposing end of the germicidal lamp is similar. An end cap, illustrated as 22 in FIG. 1, typically would cover this end portion of the germicidal lamp. However, for purposes of illustration, the end cap has been removed to better view the structure of the end of the germicidal lamp. A tubular quartz envelope 30 has a pressed portion 32 sealing an end thereof. The pressed end 32 seals the end against ribbon conductors 34. Wires 36 are electrically coupled to the ribbon conductors 34. The wires 36 extend out of the end cap, not illustrated, and are electrically connected to pins for making an electrical connection to the lamp. The electrical connection to the germicidal lamp may be of any conventional electrical connection technique. Electrode supports 38 extend into the interior of the germicidal lamp and hold a filament electrode 42. Placed on one of the electrode supports 38 may be auxiliary amalgam 40. The auxiliary amalgam 40 preferably is composed of an amalgam with a high melting point to prevent melting during the high temperatures associated with high wall loads. However, this auxiliary amalgam 40 is generally not sufficient to maintain the desired mercury vapor pressure for efficient operation of the germicidal lamp. Additionally, this auxiliary amalgam 40 may not be required but may be utilized in some applications.

Formed on the quartz envelope 30 between the sealed end 32 and the filament electrode 42 is an amalgam container 46. The amalgam container 46 may be a quartz or glass tube communicating with the interior of the quartz envelope 30. A restricted open end 50 is formed adjacent the quartz envelope 30. Amalgam 44 is placed within the amalgam container 46. The amalgam container 46 is sealed at sealed end 48. During manufacture of the germicidal lamp, the amalgam container 46 may be used to evacuate the quartz envelope 30 as well as to introduce other substances, such as an inert gas, prior to the placement of an amalgam 44 and being sealed at sealed end 48. The restricted open end 50 is sufficiently small to prevent the amalgam 44 from passing therethrough. However, the amalgam is in communication through the restricted open end 50 to the interior of the quartz envelope 30. Therefore, the mercury vapor pressure within the quartz envelope 30 may be controlled by the absorption and release of mercury by the amalgam 44. The amalgam 44 may be any conventional amalgam well known for the purpose of controlling the mercury vapor pressure in a low pressure mercury vapor gas discharge lamp. However, because the amalgam 44 is retained in the amalgam container 46, the type of amalgam 44 selected could be an amalgam that has desirable properties, but would melt at the expected high temperatures resulting from high wall loads and improved output.

FIG. 2B illustrates another view of a portion of the end of the gas discharge lamp illustrated in FIG. 2A. In FIG. 2B, the end of the gas discharge lamp is rotated 90° from the view illustrated in FIG. 2A.

Figure 3B:
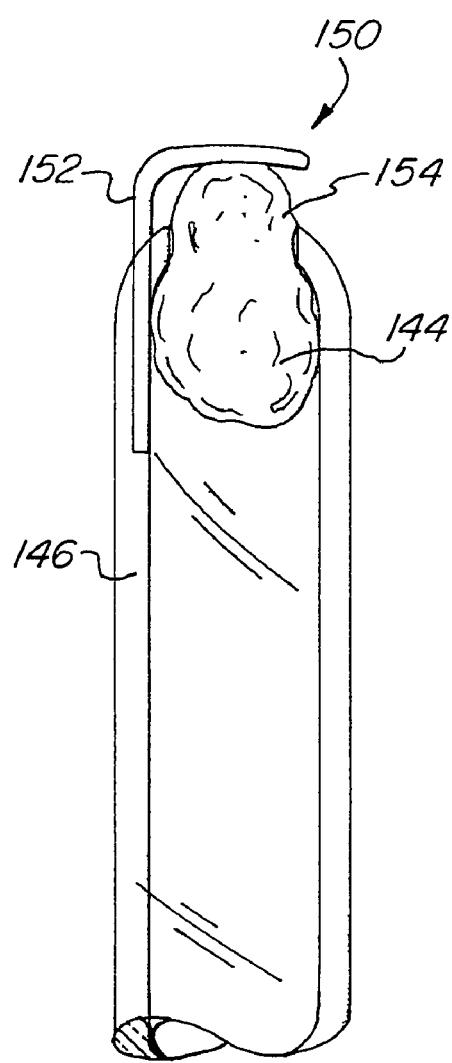
FIG. 3B is an enlarged view illustrating an amalgam container of the embodiment illustrated in FIG. 3A.
Figure 3A:
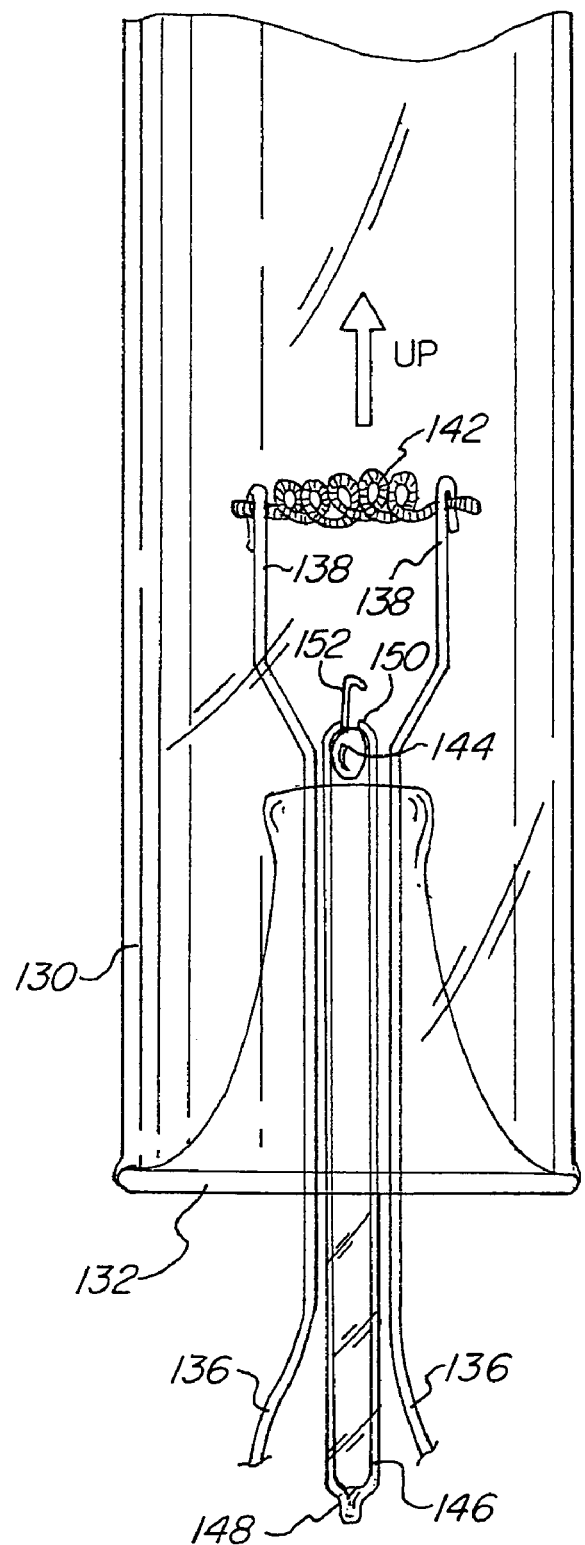
FIG. 3A is a partial view illustrating one end of a germicidal lamp according to another embodiment of the present invention.

FIGS. 3A and 3B illustrate another embodiment of an amalgam container for retaining the amalgam between the end of the lamp and the electrode. In FIG. 3A, a glass cylindrical or tubular envelope 130 has a sealing stem 132 used to seal the end of the tubular envelope 130. The sealing stem 132 has electrode supports 138 formed therein. One end of the electrode supports 138 hold a filament electrode 142 with the other end of the electrode supports 138 passing through the sealing stem 132 and are electrically coupled to wires 136. Wires 136 are electrically connected to pins, not illustrated in FIG. 3A, used to power the germicidal lamp. Formed within the sealing stem 132 is an amalgam container 146. The amalgam container 146 has a sealed end 148 and a restricted open end 150. Also formed adjacent the restricted open end 150 is a metal hook retainer 152. The combination of the restricted open end 150 and the hook retainer 152 prevents amalgam 144 from passing therethrough and into the interior of the glass tubular envelope 130. The restricted open end 150 and the hook retainer 152 are configured such that a gap formed there between is capable of retaining the amalgam even when in a fluid or liquid state. The amalgam typically being a mercury compound, generally has a property of being viscous yet capable of being retained within an opening having small enough dimensions. Accordingly, the surface of the amalgam 144 is opened to the interior of the tubular envelope 130 of the germicidal lamp, but is retained in position behind the filament electrode 142 and adjacent the end of the germicidal lamp. The amalgam container 146 may be a small tube that is also used to evacuate the interior of the germicidal lamp as well as introduce other materials, such as an inert gas, during manufacture of the germicidal lamp prior to sealing.

FIG. 3B is an enlarged view illustrating a portion of the amalgam container 146. As more clearly illustrated in FIG. 3B, the restricted open end 150 is formed by a hole 154 within the amalgam container 146 and the hook retainer 152. The hook retainer 152 may be made of a metal material that is imbedded within a side of the glass amalgam container 146. The amalgam 144 is thereby retained in position even when the germicidal lamp is held vertically during operation.

The present invention makes possible a high output mercury vapor gas discharge germicidal lamp that can be heavily loaded without overly heating an amalgam. The position of the amalgam outside of the arc path and in a cooler location behind the electrode prevents the amalgam from being overheated. Overheating of the amalgam compromises the efficient operation of the germicidal lamp. Additionally, the restriction and containing of the amalgam within the desired location makes possible operation of the germicidal lamp in a vertical position while under high load. The present invention also makes possible the efficient operation of a germicidal lamp over a relatively wide range of operating temperatures. This is particularly important when used in waste water treatment due to the range of waste water temperature. Additionally, since a higher load high output germicidal lamp is obtained with the present invention, fewer lamps are needed to achieve a desired germicidal action thereby resulting in the need for fewer lamps and resulting in lower cost. Further, maintenance costs are reduced due to the use of fewer germicidal lamps.

In another embodiment of the present invention heating and cooling control is provided for controlling the operation of the germicidal lamp. The temperature of the amalgam may be used to control the vapor pressure and therefore the operation of the germicidal lamp. Generally, it is desirable to maintain a temperature range of between seventy-five and one hundred and twenty degrees centigrade. The specific temperature will depend on the type of amalgam selected and the desired operation of the germicidal lamp. The use of temperature control of the amalgam may also be used to control the illumination output of a lamp so as to make the lamp dimmable. By controlling the temperature of the amalgam the lamp may be made dimmable by approximately ten percent.

Figure 4:
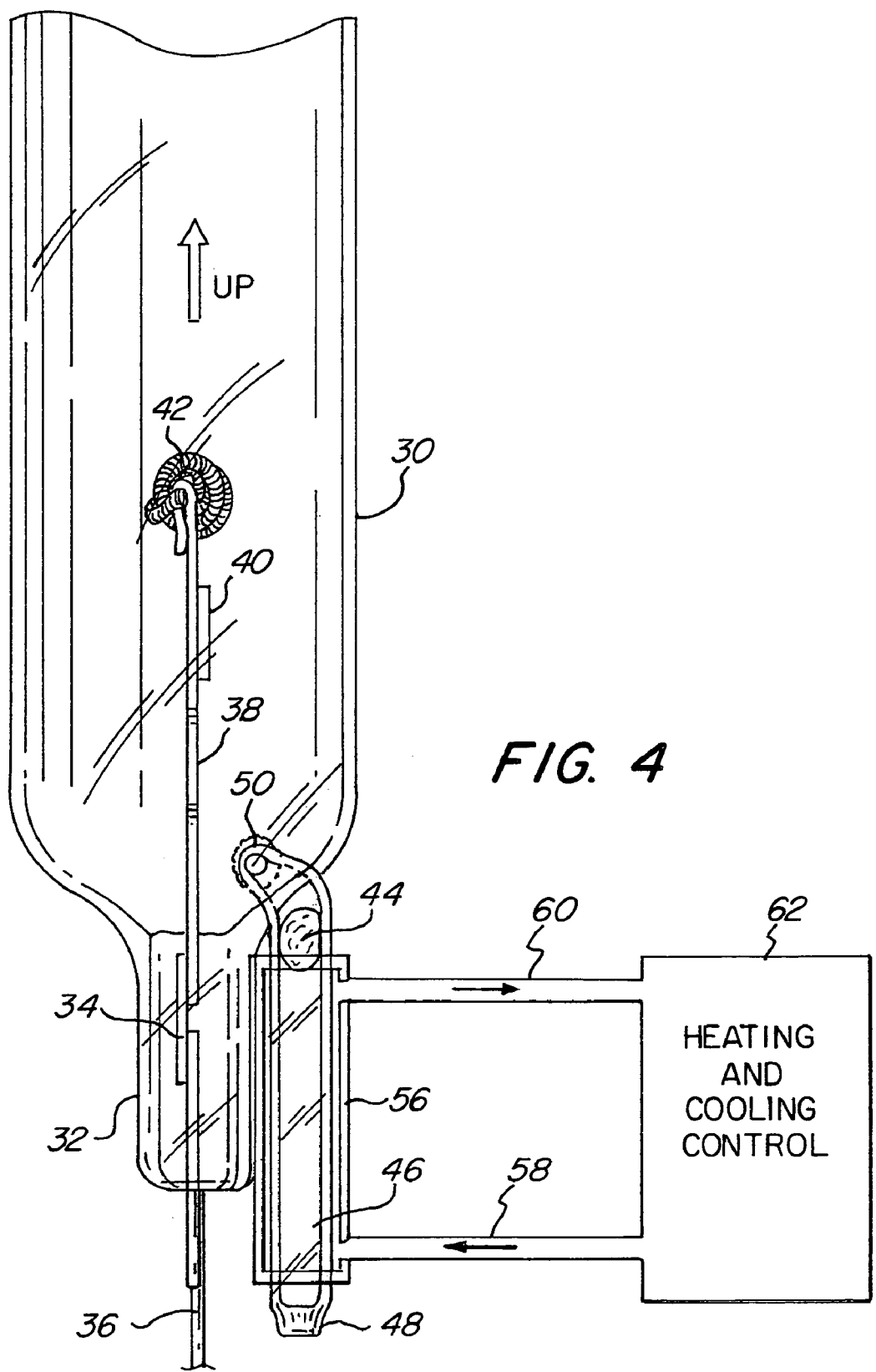
FIG. 4 is a partial view illustrating one end of a germicidal lamp according to an embodiment providing heating and cooling control of the amalgam used in the present invention.
Figure 5:
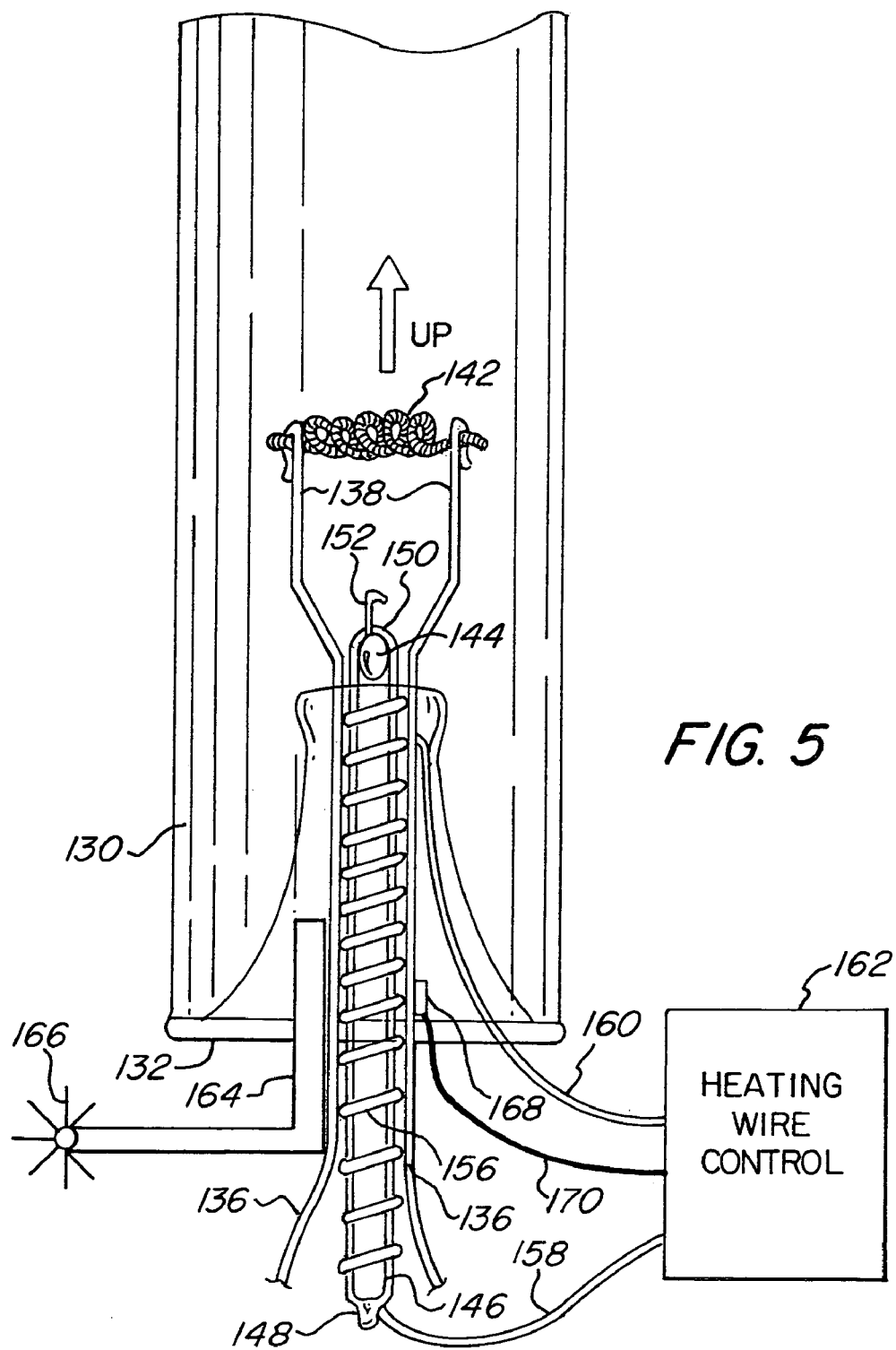
FIG. 5 is a partial view illustrating one end of a germicidal lamp according to another embodiment providing heating and cooling control of the amalgam used in the present invention.

FIGS. 4 and 5 schematically illustrate means for controlling the temperature of the amalgam in a gas discharge lamp, and in particular a germicidal lamp. These embodiments may also be used to provide a dimming feature or capability to a lamp.

FIG. 4 illustrated heating and cooling the amalgam container 46 containing the amalgam 44 by encircling the amalgam container 46 with an outer chamber 56. The outer chamber 56 may be made of glass, or any similar material. The outer chamber 56 has an attached input tube 58 and output tube 60 for providing flow of a fluid within the outer chamber 56 and around the amalgam container 46. A heating and cooling control 62 controls the temperature and flow of fluid through the input tube 58 and output tube 60 for maintaining a predetermined temperature around the amalgam container 46. Accordingly, the temperature of the amalgam 44 may be controlled so as to provide a desired vapor pressure within the envelope 30 of the germicidal lamp. The vapor pressure influences the operation of the lamp and illumination output. The remaining structure of the lamp is similar to that illustrated in FIGS. 2A and 2B.

FIG. 5 illustrates another embodiment of the present invention that controls the temperature of the amalgam with both heating and cooling. Wrapped around the amalgam container 146 is a heating wire 156. A first end 158 and a second end 160 of the heating wire 156 are coupled to a heating wire control 162. The heating wire control 162 controls the current in the heating wire 156 and therefore, its temperature. A temperature sensor 168 is placed adjacent the amalgam container 146 and is coupled with wire 170 to the heating wire control 162. A heat sink 164 is placed adjacent the amalgam container 146. The heat sink 164 may be made of a metal of high thermal conductivity. The heat sink 164 is coupled to cooling fins 166. The cooling fins 166 may be placed in a flowing fluid, such as in the application of a germicidal lamp the water being treated. The heating wire control may adjustable within a range so as to cause an illumination output of the low pressure mercury vapor discharge lamp to be variable. The remaining structure of the lamp is similar to that illustrated in FIGS. 3A and 3B.

The size and number of cooling fins 166 may be determined by the approximate cooling required to maintain the amalgam 144 within a predetermined temperature range. The heating wire control 162 and attached temperature sensor in combination with the heat sink 164 may be used to maintain the amalgam 144 contained within the amalgam container 146 at any predetermined temperature to maintain the operation of the lamp at a desired output. By changing the temperature of the amalgam 144 within the amalgam container 146, the illumination output of the lamp may be controlled and caused to vary by approximately ten percent. Therefore, the lamp may be made dimmable with the amalgam temperature control of the present invention.

Accordingly, an embodiment of the present invention utilizing means for controlling the temperature of the amalgam is beneficial in optimizing the operation of lamp. The means for controlling the temperature of the amalgam may be used to operate a germicidal lamp at high loads and output. In another application, the means for controlling the temperature of the amalgam may be used to dim the lamp or modify the illumination output of the lamp.

While the present invention has been described with respect to various embodiments, it should be appreciated by those skilled in the arts that various modifications may be made without departing from the spirit and scope of this invention.

What is claimed is:

1. A low pressure mercury vapor discharge lamp comprising:
   a tube having a first end and a second end;
   a first electrode placed in the first end of said tube;
   a second electrode placed in the second end of said tube, an arc path formed between said first and second electrodes, whereby when the low pressure mercury vapor discharge lamp is energized an arc is formed between said first and second electrodes;
   an amalgam container open to the interior of said tube;
   an amalgam retained within said amalgam container; and
   a temperature controlled device placed adjacent said amalgam container, said temperature controlled device comprising both a heating device and a cooling device,
   whereby the temperature of the amalgam is capable of being controlled by maintaining a predetermined controlled temperature around said amalgam container.

2. A low pressure mercury vapor discharge lamp as in claim 1 wherein:
   said temperature controlled device comprises,
   an outer chamber placed over said amalgam container;
   a heating and cooling control coupled to the heating and cooling device;
   an input tube connected between said outer chamber and said heating and cooling control; and
   an output tube connected between said outer chamber and said heating and cooling control,
   whereby a fluid is capable of being circulated around said amalgam container.

3. A low pressure mercury vapor discharge lamp as in claim 1 wherein:
   said heating device comprises a heating wire placed adjacent said amalgam container; and
   said cooling device comprising a heat sink having fins placed adjacent said amalgam container.

4. A low pressure mercury vapor discharge lamp as in claim 3 further comprising:
   a temperature sensor placed adjacent said amalgam container and coupled to said heating wire control.

5. A low pressure mercury vapor discharge lamp as in claim 1 wherein:
   said temperature controlled device is adjustable within a range so as to cause an illumination output of the low pressure mercury vapor discharge lamp to be variable.

6. A low pressure mercury vapor discharge lamp as in claim 1 wherein:
   said temperature controlled device is adjustable within a range so as to permit operation of the low pressure mercury vapor discharge lamp at high wall loads greater than 250 milliwatts per centimeter squared.

7. A low pressure mercury vapor discharge lamp as in claim 6 wherein:
   said low pressure mercury vapor discharge lamp comprises a germicidal lamp.

8. A low pressure mercury vapor discharge lamp comprising:
   a tube having a first end, a second end, and an interior;
   a first electrode placed in the first end of said tube;
   a second electrode placed in the second end of said tube, an arc path formed within the interior between said first and second electrodes, whereby when the low pressure mercury vapor discharge lamp is energized an arc is formed between said first and second electrodes;
   an amalgam container open to the interior of said tube;
   an amalgam retained within said amalgam container; and
   means, placed adjacent said amalgam container, for heating and cooling said amalgam,
   whereby the temperature of the amalgam is capable of being controlled by maintaining a predetermined temperature around said amalgam container resulting in the lamp being optimized or if desired becoming dimmable.

9. A low pressure mercury vapor discharge lamp as in claim 8 wherein said means for heating and cooling said amalgam comprises:
   an outer chamber placed around said amalgam container; and
   a heating and cooling control adapted to cause a fluid to circulate within said outer chamber.

10. A low pressure mercury vapor discharge lamp as in claim 8 wherein said means for heating and cooling said amalgam comprises:
    a heating wire placed adjacent said amalgam container;
    a heating wire control coupled to said heating wire;
    a heat sink placed adjacent said amalgam container.

11. A low pressure mercury vapor discharge lamp as in claim 10 further comprises:
    a temperature sensor placed adjacent said amalgam container and coupled to said heating wire control.

12. A germicidal ultraviolet low pressure mercury vapor discharge lamp having a predetermined operating temperature for use in the treatment of waste water comprising:
    an elongated glass tube having a first end and a second end and an interior and exterior wall surface;
    a first electrode placed in the first end of said elongated, glass tube;
    a second electrode placed in the second end of said elongated glass tube, an arc path formed between said first and second electrodes, whereby when the germicidal ultraviolet low pressure mercury vapor discharge lamp is energized an arc is formed between said first and second electrodes; and
    an amalgam container attached to the exterior wall surface of said elongated glass tube at the first end open to the interior and located between said first electrode and the first end of said elongated glass tube;
    an amalgam placed in said amalgam container, said amalgam having a melting point lower than the predetermined operating temperature of said germicidal ultraviolet low pressure mercury vapor discharge lamp;
    retainer means, formed on said amalgam container, for retaining said amalgam in said amalgam container when said amalgam is melted;
    heating means, placed adjacent said amalgam container, for heating said amalgam;
    cooling means, placed adjacent said amalgam container, for cooling said amalgam, whereby the germicidal ultraviolet low pressure mercury vapor discharge lamp is capable of being positioned vertically and operated at high wall loads while retaining said amalgam in the predetermined position out of the arc path and providing efficient operation of the germicidal ultraviolet low pressure mercury vapor discharge lamp over a relatively wide range of operating temperatures.

13. A germicidal ultraviolet low pressure mercury vapor discharge lamp comprising:

an elongated glass tube having a first end and a second end and an interior and exterior wall surface;

a first electrode placed in the first end of said elongated glass tube;

a first pressed end sealing the first end of said elongated glass tube;

a second electrode placed in the second end of said elongated glass tube, an arc path formed between said first and second electrodes, whereby when the germicidal ultraviolet low pressure mercury vapor discharge lamp is energized an arc is formed between said first and second electrodes;

a second pressed end sealing the second end of said elongated glass tube;

an amalgam container attached to the wall surface adjacent said first pressed end of said elongated glass tube and open to the interior located between said first electrode and the first end of said elongated glass tube;

retainer means, formed on an end of said amalgam container adjacent the wall surface, for retaining an amalgam in said amalgam container;

a heating element placed adjacent said amalgam container;

a heat sink having fins placed adjacent said amalgam container, whereby the fins may be placed in a flowing fluid such as water being treated by the germicidal ultraviolet low pressure mercury vapor discharge lamp; and a heating element control coupled to said heating element, whereby the germicidal ultraviolet low pressure mercury vapor discharge lamp is capable of being positioned vertically and operated at high wall loads while retaining the amalgam in the predetermined position out of the arc path, and the temperature of the amalgam is capable of being controlled for maintaining a predetermined temperature around said amalgam container optimizing operation of the germicidal ultraviolet low pressure mercury vapor discharge lamp during operation at high wall loads.

\* \* \* \* \*